US00PP29257P3

(12) United States Plant Patent
Stemkens

(10) Patent No.: US PP29,257 P3
(45) Date of Patent: Apr. 24, 2018

(54) ***SAXIFRAGA* PLANT NAMED 'SAXZ0016'**

(50) Latin Name: *Saxifraga×arendsii*
Varietal Denomination: SAXZ0016

(71) Applicant: SYNGENTA PARTICIPATIONS AG, Basel (CH)

(72) Inventor: Henricus Godefridus Wilhelmus Stemkens, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/330,086

(22) Filed: Aug. 3, 2016

(65) Prior Publication Data

US 2017/0135268 P1 May 11, 2017

Related U.S. Application Data

(60) Provisional application No. 62/252,750, filed on Nov. 9, 2015.

(51) Int. Cl.
*A01H 5/02* (2018.01)

(52) U.S. Cl.
USPC ..... Plt./263.1

(58) Field of Classification Search
USPC ..... Plt./263.1
See application file for complete search history.

(56) References Cited

PUBLICATIONS

PLUTO: Plant Variety Database, Sep. 9, 2017, citation for 'SAXZ0016'. 1 page.*

* cited by examiner

*Primary Examiner* — Susan McCormick Ewoldt
*Assistant Examiner* — Karen M Redden
(74) *Attorney, Agent, or Firm* — Dale Skalla

(57) ABSTRACT

A new *Saxifraga* plant named 'SAXZ0016' particularly distinguished by the blushed red-purple flower color with a darker eye, short peduncles on a vigorous plant habit, and is very early to mature and flower.

1 Drawing Sheet

Latin name of the genus and species of the plant claimed: *Saxifraga×arendsii.*

Varietal denomination: 'SAXZ0016'.

BACKGROUND OF THE NEW PLANT

The present invention comprises a new *Saxifraga*, botanically known as *Saxifraga×arendsii*, and hereinafter referred to by the variety name 'SAXZ0016'.

'SAXZ0016' is a product of a planned breeding program. The new cultivar 'SAXZ0016' has large blushed red-purple flower color with a darker eye, short peduncles on a vigorous plant habit and is very early to mature and flower.

'SAXZ0016' originates from a hybridization made in a greenhouse in April 2008 in Enkhuizen, The Netherlands. The female parent was an unpatented, proprietary plant identified as 'H1347-57', with smaller flowers, darker pink color and is later to flower when compared to 'SAXZ0016'.

The male parent of 'SAXZ0016' was a patented (U.S. Plant Pat. No. 24,362), proprietary plant identified as 'SAXZ0008', with smaller flowers and a light pink color with a deeper pink eye and is later to mature and flower when compared to 'SAXZ0016'. The resultant seed was sown in August 2008 in Enkhuizen, The Netherlands.

'SAXZ0016' was selected as one flowering plant within the progeny of the stated cross in March 2009 in a greenhouse in Enkhuizen, The Netherlands.

The first act of asexual reproduction of 'SAXZ0016' was accomplished when vegetative cuttings were propagated from the initial selection in March 2009 in a greenhouse in Enkhuizen, The Netherlands.

BRIEF SUMMARY OF INVENTION

Horticultural examination of plants grown from cuttings of the plant initiated in March 2009 in Enkhuizen, The Netherlands, and continuing thereafter, has demonstrated that the combination of characteristics as herein disclosed for 'SAXZ0016' are firmly fixed and are retained through successive generations of asexual reproduction.

'SAXZ0016' has not been observed under all possible environmental conditions. The phenotype may vary significantly with variations in environment such as temperature, light intensity and day length.

A Plant Breeder's Right for this cultivar was applied for in the European Union on Jul. 1, 2015, No. 2015/1545. 'SAXZ0016' has not been made publicly available prior to the effective filing date of this application, notwithstanding any disclosure that may have been made less than one year prior to the effective filing date of this application by the inventor or another who obtained 'SAXZ0016' directly from the inventor.

The following traits have been repeatedly observed and are determined to be basic characteristics of the new variety. The combination of these characteristics distinguishes this *Saxifraga* as a new and distinct variety.

BRIEF DESCRIPTION OF THE PHOTOGRAPHS

The accompanying photographic drawings show typical flower and foliage characteristics of 'SAXZ0016' with colors being as true as possible with an illustration of this type.

Figure 1:
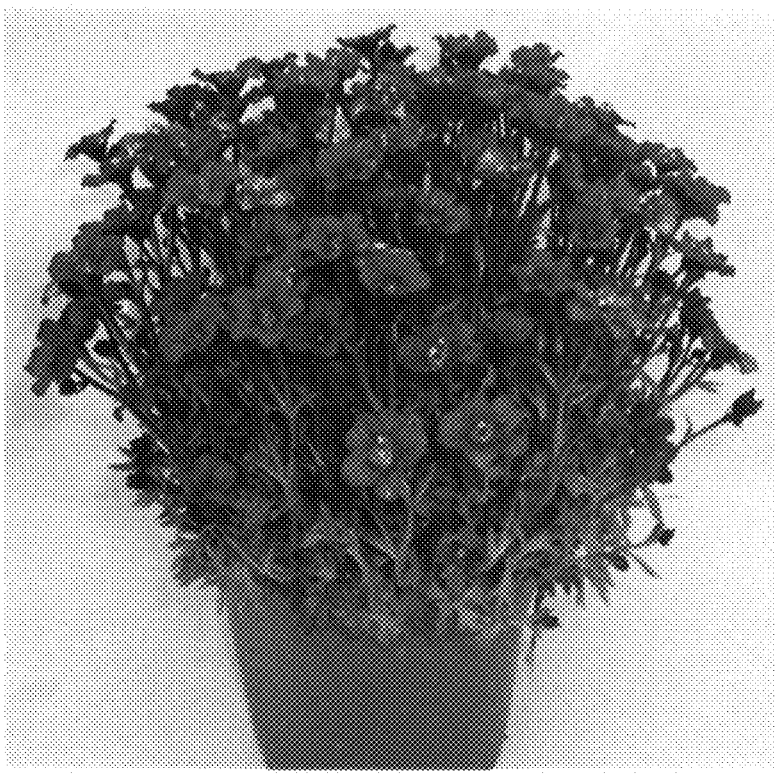
Figure 2:
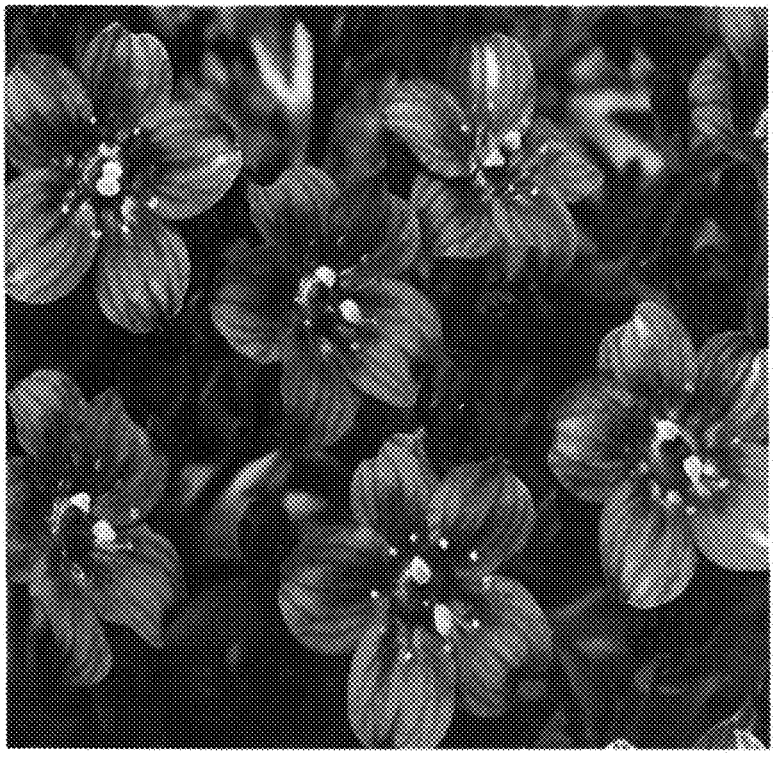

The photographic drawings show in FIG. 1 shows a flowering plant of the new variety and FIG. 2 shows a close-up of the flowers.

DETAILED BOTANICAL DESCRIPTION

The plant descriptions and measurements were taken in Enkhuizen, The Netherlands under natural light in March 2015. These plants were approximately 34 weeks old and were growing in 12 cm pots in hoop house trials. The plants used for the photographs were about 34 weeks old growing in Enkhuizen, The Netherlands and the photographs were taken in March 2014.

Color chart used: Royal Horticultural Society Colour Chart (R.H.S.) 2001

TABLE 1

DIFFERENCES BETWEEN THE NEW VARIETY 'SAXZ0016' AND A SIMILAR VARIETY

| | 'SAXZ0016' | 'ROCKLET', U.S. Plant Pat. No. 19,000 |
|---|---|---|
| Flower color: | Deep rose | Scarlet |
| Earliness: | Earlier | Later |
| Leaves shape: | Narrow, thin | Thick, broad |
| Flower and petal size: | Bigger | Smaller |

Plant:

*Form, growth and habit*.—A rosetting habit that is very compact and mounded. Each rosette develops several short branched peduncles that are freely flowering.

*Plant height*.—6 cm.

*Plant height* (*inflorescence included*).—10 cm.

*Plant width*.—14 cm.

Roots:

*Number of days to initiate roots*.—About 7 days at 18 degrees C.

*Number of days to produce a rooted cutting*.—3 weeks at 18 degrees C.

*Type*.—Fine, fibrous, free branching.

*Color*.—RHS N155B but whiter.

Foliage:

*Arrangement*.—Alternate.

*Immature, leaf color, upper surface*.—RHS 137B.

*Immature, leaf color, lower surface*.—RHS 138A.

*Mature, leaf color, upper surface*.—RHS 137B.

*Mature, leaf color, lower surface*.—RHS 138B.

*Length*.—1.7 cm.

*Width*.—1.7 cm.

*Shape*.—Cuneate; 3 to 5 cleft-lobed.

*Base shape*.—Attenuate.

*Apex shape*.—Acute.

*Margin*.—Entire.

*Texture, upper surface*.—Pubescent, long hair of 0.2 cm.

*Texture, lower surface*.—Pubescent, short hair.

*Color of veins, upper surface*.—Indistinct.

*Color of veins, lower surface*.—Indistinct.

*Petiole color upper surface*.—RHS 143C.

*Petiole color lower surface*.—RHS 143C.

*Length*.—0.5-0.7 cm.

*Diameter*.—0.4-0.5 cm.

*Texture*.—Glabrous except on edges, long hair up to 0.3 cm.

Lateral branching:

*Color*.—RHS N144B.

*Length of branch*.—0.5-5 cm.

*Diameter of branch*.—0.1-0.2 cm.

*Texture*.—Glabrous.

*Color of peduncle*.—RHS 144B.

*Length of peduncle*.—4.0-6.0 cm.

*Peduncle diameter*.—0.2 cm.

*Texture*.—Heavily covered with glandular hairs.

*Hair color*.—White, RHS 155A and gland part is RHS 61A.

*Pedicel color*.—RHS 144B.

*Pedicel length*.—1.5-2 cm.

*Pedicel diameter*.—0.1-0.2 cm.

*Pedicel texture*.—Heavily covered with glandular hairs.

*Hair color*.—White, RHS 155A and gland part is RHS 61A.

Inflorescence:

*Type*.—Out of each rosette (whorl of leaves) 1-3 branched inflorescences emerge, each inflorescence consist of 2-15 single flowers. Simple cyme or raceme; flowers held above the plant and very flat.

*Quantity of inflorescences per plant*.—45-100 with numerous buds.

*Lastingness of individual blooms on the plant*.—About 11 days.

*Fragrance*.—None.

Bud: (just before opening/showing color):

*Color*.—Mix of RHS 60A/RHS N186C.

*Length*.—0.7 cm.

*Width*.—0.5 cm.

*Shape*.—Orbicular.

Corolla:

Immature inflorescence:

*Diameter*.—1.5 cm.

*Color of petals, upper surface*.—RHS 66A, very deep with veins of RHS 59A.

*Color of petals, lower surface*.—RHS 60B-C ground color with veins of RHS 183A.

Mature inflorescence:

*Flower diameter*.—2.3-2.5 cm.

*Depth*.—1.2 cm.

*Petal color, upper surface*.—RHS N66A, deep, with base and veins of RHS 59A.

*Petal color, lower surface*.—RHS N60B with veins of RHS 183A.

*Veins color, upper surface*.—RHS 59A.

*Veins color, lower surface*.—RHS 183A.

*Length of petal*.—1.0-1.2 cm.

*Width of petal*.—1.0-1.2 cm.

*Shape*.—Orbicular.

*Apex shape*.—Broadly rounded to some broadly.

*Margin*.—Entire.

*Venation pattern*.—Bowed.

*Petal texture, upper surface*.—Papillose.

*Petal texture, lower surface*.—Papillose.

Calyx:

*Quantity*.—5.

*Color, upper surface*.—RHS 147B.

*Color, lower surface*.—RHS 147B.

*Length*.—0.4-0.5 cm.

*Width*.—0.3 cm.

*Shape*.—Lanceolate.

*Apex shape*.—Acute.

*Base*.—Fused.
*Margins*.—Entire.
*Texture, upper/inner surface*.—Smooth, glabrous.
*Texture, lower/outer surface*.—Glandular hairs, much more on the fused part.

Reproductive organs:
*Gynoecium*.—
*Pistil quantity*.—1.
*Pistil shape*.—One style divided in 2 lobs at the stigma.
*Length*.—0.3-0.4 cm.
*Style color*.—RHS 199A.
*Style length*.—0.20 cm.
*Stigma color*.—RHS 163C.
*Stigma shape*.—Bi-parted.
*Ovary color*.—RHS N144B.
*Ovary height*.—0.4 cm.
*Ovary width*.—0.5 cm.
*Androecium*.—
*Stamens, quantity*.—10.
*Stamens, shape*.—Threadlike.
*Color of filaments*.—RHS 185B.
*Length filaments*.—0.4 cm.
*Anther color*.—RHS 22C, mottled with anthocyanins of about RHS N34C.
*Anther length*.—0.05 cm.
*Anther shape*.—Oval.
*Color of pollen*.—RHS 2A.
*Pollen amount*.—Very little.
*Fertility/seed set*.—Neither seed nor fruit production has been observed to date.
*Disease/pest resistance*.—Resistance to pathogens and pests common to *Saxifraga* has not been observed.
*Drought tolerance and cold tolerance*.—Hardy perennial. Tolerates high temperature to at least 30 degrees C. Tolerates low temperatures to minus 15 degrees C. No specific drought tolerance has not been observed.

What is claimed is:

1. A new and distinct variety of *Saxifraga* plant named 'SAXZ0016' substantially as illustrated and described herein.

* * * * *